(12) United States Patent
Hyson

(10) Patent No.: US 7,186,260 B2
(45) Date of Patent: *Mar. 6, 2007

(54) MEDICATED WRAP

(76) Inventor: Morton I. Hyson, 2020 Goldring # 402, Las Vegas, NV (US) 89106

( * ) Notice: Subject to any disclaimer, the term of this patent is extended or adjusted under 35 U.S.C. 154(b) by 695 days.

This patent is subject to a terminal disclaimer.

(21) Appl. No.: 09/936,075

(22) PCT Filed: Apr. 27, 2001

(86) PCT No.: PCT/US01/13662

§ 371 (c)(1),
(2), (4) Date: Jul. 16, 2002

(87) PCT Pub. No.: WO01/80797

PCT Pub. Date: Nov. 1, 2001

(65) Prior Publication Data

US 2003/0139698 A1    Jul. 24, 2003

Related U.S. Application Data

(63) Continuation-in-part of application No. 09/561,170, filed on Apr. 27, 2000, now Pat. No. 6,313,370.

(60) Provisional application No. 60/131,857, filed on Apr. 29, 1999.

(51) Int. Cl.
*A61B 17/00* (2006.01)

(52) U.S. Cl. ......................................... 606/204; 602/48
(58) Field of Classification Search ................ 606/204, 606/204.15–55, 201; 602/41–48, 60–64, 602/53; 604/46
See application file for complete search history.

(56) References Cited

U.S. PATENT DOCUMENTS

| | | | | |
|---|---|---|---|---|
| 5,660,854 A | * | 8/1997 | Haynes et al. | 424/450 |
| 5,695,520 A | * | 12/1997 | Bruckner et al. | 606/204 |
| 6,074,413 A | * | 6/2000 | Davis et al. | 607/108 |
| 6,143,946 A | * | 11/2000 | Docter | 602/41 |
| 6,313,370 B1 | * | 11/2001 | Hyson | 602/48 |

* cited by examiner

*Primary Examiner*—(Jackie) Tan-Uyen T. Ho

(57) ABSTRACT

A device for treating pain in an injured body member includes a wrap having an interior section which can be loaded with medicament. The wrap also includes at least one inwardly extending nodule adapted to exert pressure on and compress a specific area of the injured member, having acupressure like effect in producing pain relief. The wrap has adjustable means for fastening the wrap around the body member, thereby enabling the wearer to extent a specific amount of pressure on the nodule to achieve the desired results. The combination of restricted movement imparted by the wrap along with the medicament and acupressure affords the wearer more rapid pain relief than any of the treatments applied separately.

42 Claims, 3 Drawing Sheets

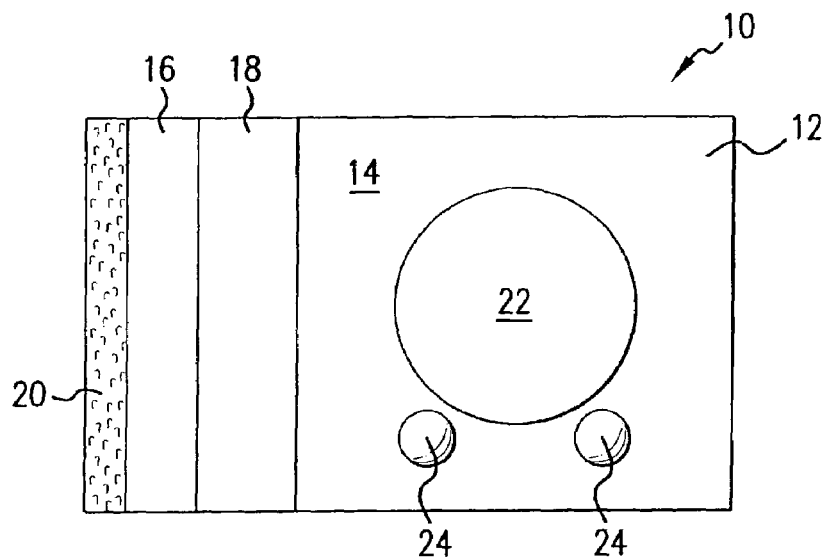
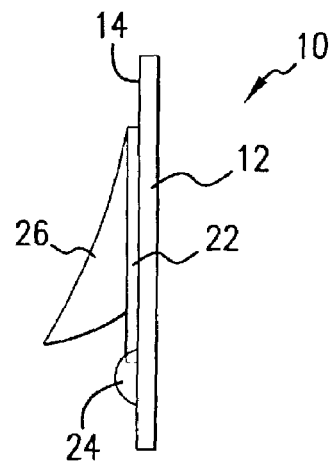
FIG.1
FIG.3
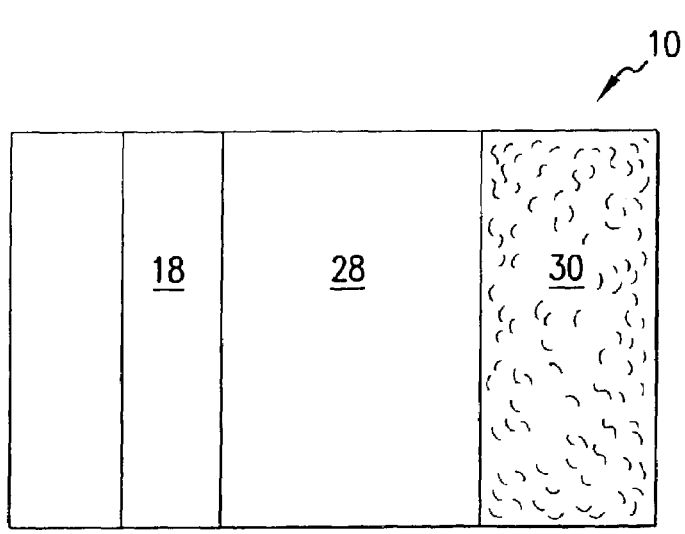
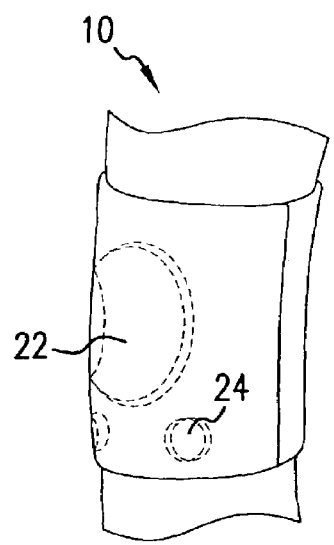
FIG.2
FIG.4

MEDICATED WRAP

This is a continuation-in-part of U.S. application Ser. No. 09/561,170, filed Apr. 27, 2000, which claims the benefit of U.S. Provisional Application Ser. No. 60/131,857, which was filed Apr. 29, 1999, the disclosures and contents of which are hereby incorporated by reference in their entireties.

FIELD OF THE INVENTION

The present invention relates to a medical device for relieving pain by simultaneously restricting movement of a body member, applying pain-relieving medicament, and applying pressure to acupressure points.

BACKGROUND OF THE INVENTION

Many people suffer from sprains, arthritis and other ailments at the joints such as the knees, elbows, wrists as well as neck pain. Often the treatment consists of wraps to stabilize and provide pressure to the joint, sports ointments and creams as well as prescribed and over-the-counter pain medications.

Many people suffering from such ailments are reluctant to take pain killing drugs over an extended period of time for fear of obtaining a dependency or simply based upon a general reluctance to take drugs. For these people, the remedies are limited to treatment through ice, heat, wraps and externally applied ointments such as sports creams and the like. The products such as wraps and ointments must be separately purchased. Further, the ointments and creams, if applied underneath a wrap, can stain and soil the wrap making it unsightly for the person to wear in public.

Still further, it is known that certain pressure joints near joints, if pressure is applied, can help to reduce and alleviate pain. The wraps and ointments heretofore used do not provide a means to impose an acupressure effect to help reduce pain.

Thus there is a clear need in the art to overcome these drawbacks.

SUMMARY OF THE INVENTION

The present invention relates to a device to be disposed around a body portion of a person for treating pain that body portion, wherein the device comprises a wrap having an interior surface for contacting the body portion, and adapted to be disposed around the body portion, said wrap being sufficiently elastic to enable the wrap to be stretched around the body portion to restrict the mobility of the body portion, at least one pad section secured to an interior section of the wrap, each pad section adapted to be loaded with medicament, at least one nodule extending inwardly from the interior surface of the wrap and adapted to contact and exert pressure at a desired specific location on the body portion, and means for tightening and adjustably securing the wrap about the body portion, whereby tightening of the wrap causes medicament to exert pressure on and dispense medicament to the area of plain, and to cause the nodule to exert pressure upon the body portion.

The present invention further relates to A method of relieving pain in a body portion comprising extending a flexible wrap around the injured body portion, said wrap having a pad section loaded with medicament and at least one substantially rigid nodule extending inwardly and adapted to contract at least one pre-located acupressure point near the area of the pain, locating the nodule above the acupressure point, and tightening and adjustably securing the wrap such that mobility of the body portion is decreased, pressure is exerted by the nodule on the desired acupressure point, and medicament is dispensed to the are of pain.

BRIEF DESCRIPTION OF THE DRAWINGS

FIG. 1 is a bottom view of a wrap according to one embodiment of the present invention adapted for joints as knees and elbows as well as the back;

FIG. 2 is a top view of he wrap of FIG. 1;

FIG. 3 is a side view of the wrap of FIG. 1;

FIG. 4 is a view of the wrap of FIG. 1 applied around a knee;

DETAILED DESCRIPTION OF THE INVENTION

Figure 5:
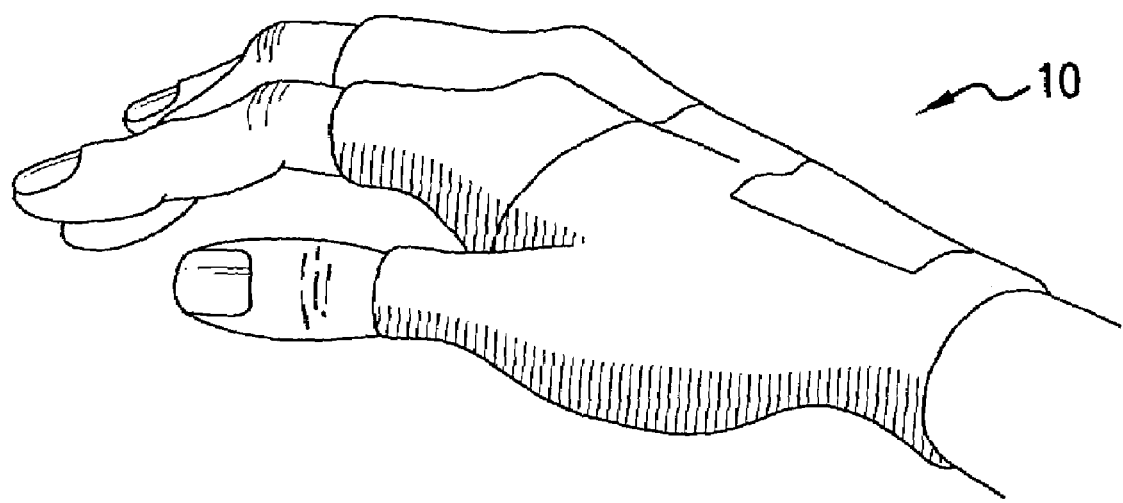
FIG. 5 is a wrap according to another embodiment of the present invention for treatment of the wrist.

The invention provides a device for treating pain in an injured body portion which includes a flexible, elastic wrap which can be secured in place around the body portion. The wrap has an interior surface which includes an absorbent pad section designed to be loaded with medicament. The pad section can come preloaded with medicament, in which case the pad is covered by a removable impervious cover element. At least one, and preferably at least two, substantially rigid nodules project inwardly from the wrap and are disposed to contact predetermined areas of the injured member. The nodules are located strategically to provide acupressure-like force against specific acupressure points, which are well known in the art, thereby compressing the point and providing additional pain relief. See, for example, U.S. Pat. Nos. 5,792,176, and 5,224,469, which disclose devices for the application of pressure ("acupressure") to selected points on the surface of the body which correspond to acupuncture points identified in Eastern medical practice.

The wrap has adjustable fastening means, such as VELCRO hook and loop fasteners, so that the user can stretch the wrap around the injured part and adjust the pressure so as to dispense medicament to the affected area and to select the desired pressure at the acupressure points.

Turning to the drawings, FIG. 1 shows a wrap 10 according to one embodiment of the present invention. The wrap 10 has an underside 12 adapted to be positioned against the skin when the wrap is used to treat a joint such as a knee or elbow or it can be of a size to wrap about the trunk of the body to treat the back. The wrap itself includes a main panel 14 connected to a side panel 16 by an elastic margin 18. At the end of the side panel 16 is one member 20 of a hook and pile fastener for securing the wrap 10 about the joint. Disposed on the body 14 is a pad 22 adapted to receive and store medicament for treatment of pain.

As shown in FIG. 3, if the pad 22 is loaded with the medicament by the manufacturer, a tearaway cover sheet 26 may be provided by which the user may tear away the protective cover to expose the pad 22 loaded with the medicament. The use of a tear-away cover is conventional technology.

The wrap 10 may also include one or more acupressure nodules 24 located to engage pressure points in the joint, muscle or ligament area to apply pressure thereto for the treatment of pain. As shown in FIG. 3, these nodules 24 may be spherical in shape and may be manufactured from a rigid product such as rubber, plastic or the like.

With reference to FIG. 2, at the top side 28 of the wrap 10 there is located the other member 30 for the hook and pile fastener for the wrap 10. Accordingly, and with reference to FIG. 4, the user would remove the protective strip or cover 26 to expose the pad 22 preloaded with medicament. The user would then place the pad 22 over, for example, the patella and position the wrap 10 about the knee joint securing it thereto using the members 20,30 of the hook and pile fastener. The elastic margin 18 enables the user to exert pressure by constricting or releasing the pressure imposed by the wrap 10 on the knee joint. In this position, as suggested in FIG. 4, the nodules 24 are disposed to the side and below the patella to exert acupressure effect on the ligaments of the knee joint.

Figure 6:
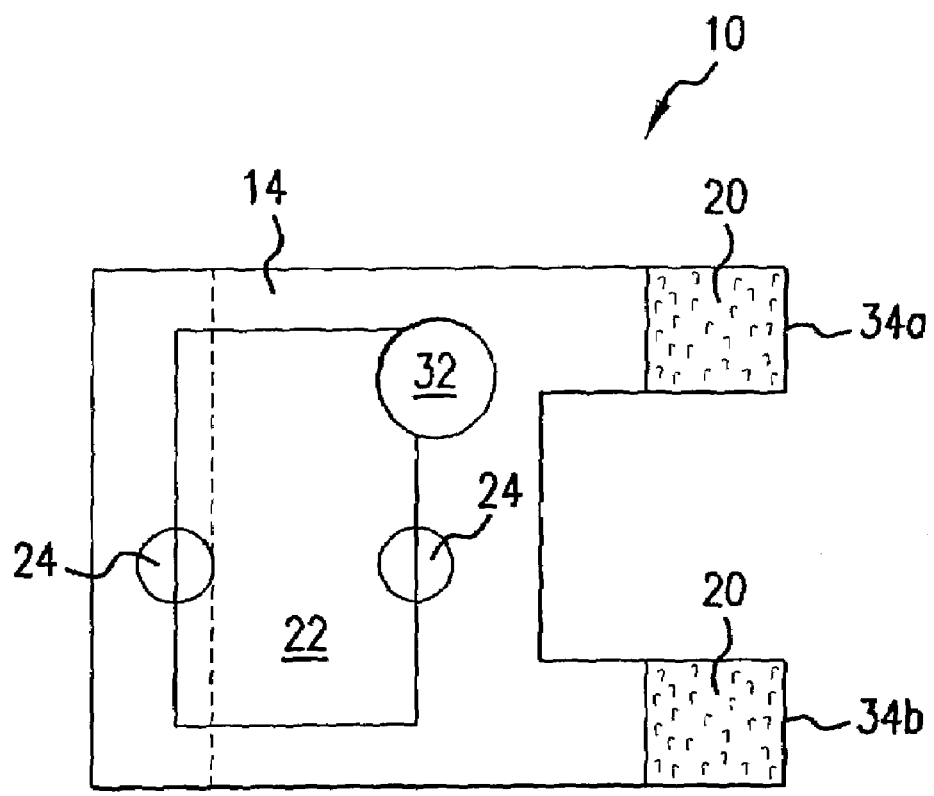
FIG. 6 is the view of the underside of the wrap of FIG. 5.

Turning to FIGS. 5 and 6, a further embodiment of the wrap 10 for use at the wrist is shown. The wrap 10 includes the main panel 14 including the pad 22 to receive the medicament. A hole 32 is provided to pass the thumb when the wrap 10 is disposed about the wrist. Acupressure nodules 24 are provided to exert pressure at desired locations on the wrist. Straps 34a, b include the one member 20 of a hook and pile fastener, the other member 30 (not shown in FIGS. 5 and 6) of the hook and pile fastener is disposed on the outside surface of the wrap 10.

Figure 7:
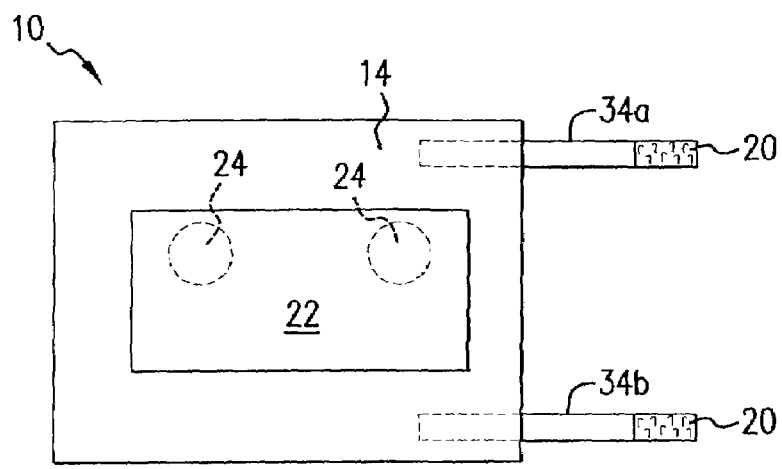
FIG. 7 is the view of the underside of a wrap according to yet another embodiment of the present invention directed for use around the neck to treat the cervical area.
Figure 8:
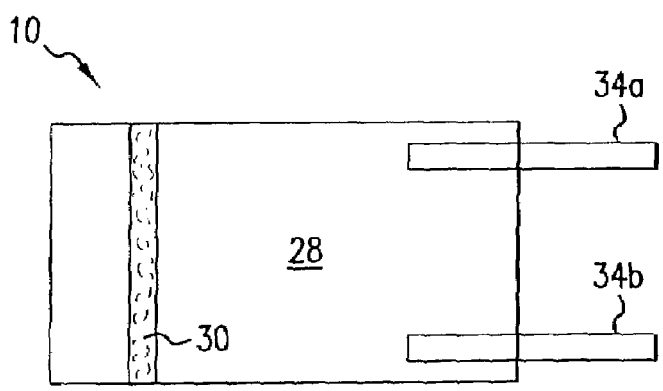
FIG. 8 is a view of the top of the wrap of FIG. 7.
Figure 9:
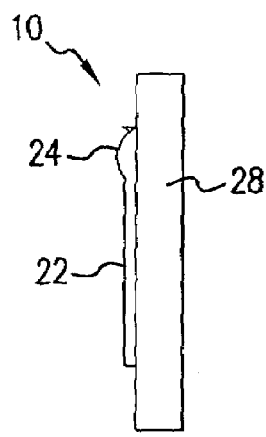
FIG. 9 is a side view of the wrap.

Turning to FIGS. 7–9, an embodiment of the wrap 10 for cervical use is disclosed. The wrap 10 includes the main panel 14 having the pad 22 to retain the medicament. Acupressure nodules 24 are provided to exert pressure at desired locations at the neck. The top side 28 includes the other member 30 of the hook and pile fastener. Straps 34a,b include the member 20 for the hook and pile fastener. Accordingly the wrap 10 is wrapped about the neck placing the pad 22 at the desired location to apply the medicament.

At least one nodule is provided on the interior of each wrap, and can be molded, sewn, welded, or otherwise secured to the interior surface of the wrap. The nodules are located on specific portions of the wrap in predetermined areas designed to correspond with known acupressure points for that specific body portion. These acupressure points as well-known and readily identifiable from medical literature, and may be adjacent areas of pain rather than directly on the pain. The nodules should be generally rigid, so that pressure can be applied quite specifically to the desired region of the member in which pain is being suffered. The nodules should have a generally curved surface, so as to not be pointed or have other sharp edges or protrusions that could injure the patient. The specific size of the nodule is not critical, although the area contacting the body should be sufficiently large so as to not create additional pain (e.g. by puncturing or sharply compressing the skin), but should not be so large as to distribute the pressure over a wider area than is necessary. Generally speaking, the area being compressed should be approximately ¼–¾ in diameter, depending on the specific area of the body involved. Examples of suitable nodules would be spherical lugs having diameter of ¼–¾ inch, preferably about ½ in though other shapes and dimensions may be usable depending upon the specific body part. For example, smaller nodules would be used for a wrist wrap, whereas larger nodules might be used for wraps for the knee or back. The nodules can be made from a generally rigid material such as hard rubber, but may have a small amount of resiliency (e.g. less than 10%) which could provide some patient comfort while not compromising the ability of the nodules to exert pressure.

The method of pain relief afforded by the invention is implemented by a user either loading the absorbent pad with a medicament or removing the plastic impervious cover to expose pre-loaded medicament. Next, the user (or someone who assists the user) extends the wrap around the injured body portion, locating the nodules above the desired acupressure points. Then the wrap is tightened until the nodules exert pressure at the desired location which is sufficient to substantially compress the desired spot yet not cause additional pain. At this point, the adjustable fastening members are attached to retain the desired pressure. The tightened wrap restricts the mobility of the injured limb, thereby promoting healing. Furthermore, the tightened pressure is sufficient to exert force on the acupressure point and exude medicament from the pad into the area of treatment. These three desired affects combined enable the wearer to heal more quickly in a pain-free environment.

After wearing the wrap for a certain period of time, the user may become accustomed to the pressure of the acupressure nodules and desire to increase the pressure, thereby increasing the effectiveness of the nodules. The releasable fastener is then released, the wrap is tightened, and the adjustable fastening members are re-attached.

The pad may be any sort of absorbent material, such as sponge, cotton or synthetic fiber, or any other known material which can hold a fluid product. The wrap may be disposable, or may be reusable in which case the pad can be reloaded by the user with medicament prior to each use.

The present invention provides a method for pain relief comprising topical administration of therapeutic medicaments using the device disclosed herein. Although topical administration of a medicament avoids, inter alia, many of the drawbacks of oral administration of pain medication, a topical administered medicament must overcome the complex set of diffusion barriers provided by the skin. In general, the skin is highly resistant to permeation by chemicals, including drugs. Although the skin is only a few millimeters thick, the stratum corneum serves as a highly protective barrier against physical, chemical and bacterial penetration. This barrier primarily consists of dead skin cells bound together by certain fatty (lipid) materials. Generally, only drugs that are effective in the body at very low concentrations or that have particular physical properties have been successfully delivered through the skin in therapeutically effective amounts. High molecular weight drugs and drugs which are either charged or highly polar can be difficult to administer transdermally.

Accordingly, the rate of penetration of such a topically-applied medicament is dependent upon a number of variables including: the bodily area to which the medicament is applied, the concentration of the active ingredient or ingredients of the applied medicament, and the nature of the vehicle, if any, containing the active ingredient or ingredients of the medicament. The nature of the vehicle selected is defined by, for example, the solubility of the active ingredient and/or active ingredients in the vehicle, rate of release of the active ingredient or active ingredients from the vehicle, the facility with which the vehicle hydrates the stratum corneum layer of the skin and thereby improves permeability of the skin barrier to the active ingredient and/or active ingredients, and the stability of the active ingredient and/or active ingredients in the vehicle. The choice of vehicle for dissolution or suspension of the active ingredient or ingredients is well known in the art (See, for example, Dirk B. Robinson and Howard I. Miabach, *Dermatologic Pharmacology* in BASIC AND CLINICAL PHARMACOLOGY, 871–87 (Bertram G. Katzung, Ed., Fifth Edition, 1992), which is hereby incorporated by reference in its entirety). The presence of one or more penetration enhancers, described below, in the medicament also affects the rate of diffusion of the one or more active ingredient of the medicament into and across the skin barrier.

The pad section may comprise, in various embodiments of the invention, one or more of the following elements: a backing film, a polymer matrix formulated with the active ingredient and/or a compartment filled with a vehicle comprising one or more active ingredients and, in certain embodiments, the vehicle may comprise one or more excipients, one or more membranes that control the rate of release of the active ingredient, pressure-sensitive adhesives that, in certain embodiments, comprise at least one active ingredient and may further comprise at least one excipient, an absorbent material such as, but not limited to, a cotton pad or a sponge, a protective, pressure-sensitive release liner, and a removable impervious cover element.

The backing film used in the pad section has an inner surface and an outer surface. The outer surface of the backing film is attached to the inner surface of the wrap. The composition of the backing film is selected according to, inter alia the nature of the active ingredient to be delivered and the length of time the wrap is to remain attached to the body. In certain embodiments, the backing film is constricted of a synthetic polyester to facilitate hydration of the outer surface of the skin. In other embodiments, the backing film is constructed of, as non-limiting examples, polyurethane or polyolefin polymers, and woven or non-woven fibrous materials such as cotton or polyesters and blends thereof. In certain embodiments, the backing film is the inner surface of the wrap.

The removable impervious cover element has an inner and outer surface. The edges of the inner surface of the cover element can be attached to the edges of the inner surface of the backing film, thereby forming a space within which the medicament is disposed. The removable impervious cover element is generally constructed of a thin (0.002–0.005 inch) impermeable material, which, in one non-limiting example, is a polyester film. The adhesive used for attaching the removable impervious cover element to the backing film is, in one non-limiting example, a silicone-based, pressure-sensitive adhesive release polymer.

In certain embodiments of the invention, a membrane, which controls release of the medicament and/or the active ingredient thereof, referred to herein as a rate-controlling membrane is disposed between the removable impervious cover and the medicament. The rate controlling membrane has an inner and an outer surface, wherein the inner surface is in contact with the medicament and the outer surface is the surface to be placed in contact with the skin of the subject patient. The rate-controlling membrane, when present, is generally constructed of, inter alia, a thin (0.001–0.003 inch) film of ethylene vinyl acetate or polyethylene.

In certain embodiments of the invention, a pressure-sensitive adhesive comprising the one or more active ingredients, is disposed between the backing film and the removable impervious cover, or, when the pad section comprises a rate-controlling membrane, between the backing film and the rate-controlling membrane. In certain embodiments of the invention, the pressure-sensitive adhesive is a hydrophilic adhesive hydrogel, which is formed, in one non-limiting example, from high molecular weight polyvinylpyrrolidone and oligomeric polyethylene oxide.

Accordingly, in one embodiment of the invention the medicament is formulated as a hydrogel. Hydrogels are well known in the art as vehicles for the controlled release of drugs. For example, N. A. Peppas, Ed, *Hydrogels in Medicine and Pharmacy* CRC Press, Inc. (1987) Vol. II, discloses the use of water soluble cellulose ethers such as methylcellulose for controlled release drug delivery systems.

In another embodiment of the present invention, the adhesive hydrogel comprises water soluble polymers such as cellulose. Such adhesive hydrogels are described in U.S. Pat. Nos. 5,344,655 and 5,254,338, which are hereby incorporated by reference in their entirety. In a further embodiment, the adhesive hydrogel comprises an aqueous mixture of a radiation crosslinkable water-soluble polymer such as a polymer of N-vinyl-2-pyrrolidone and ethylene oxide and a humectant such as propylene glycol which may be incorporated within the pad section of the medicated wrap of the present invention. The hydrogel may also contain preservatives such as propyl paraben and methyl paraben. Such adhesive hydrogels are described in U.S. Pat. No. 5,405,366, which is hereby incorporated by reference in its entirety.

In another embodiment of the present invention, the skin-compatible, pressure-sensitive adhesive hydrogel comprises polyvinyl pyrrolidone and polyvinyl alcohol, a polar plasticizer or humectant such as propylene glycol, water and at least one active ingredient. The composition may also contain cellulose derivatives to increase strength and guar gum to increase tackiness. Such adhesive hydrogels are described in U.S. Pat. No. 4,593,053, which is hereby incorporated by reference in its entirety.

In another embodiment, the adhesive hydrogel comprises a water-absorbent resin such as a vinyl acetate-acrylic acid ester copolymer that swells to form a hydrogel upon contact with water. In this instance, the medicament is formulated as a dry powder comprising a gelling agent and at least one active ingredient, where the gelling agent comprises, in one non-limiting example, methylcellulose, a natural gum, glucose, propylparben, methylparaben, and sodium chloride. In other embodiments, the adhesive hydrogels of the present invention further comprise a substituted urea of the formula R—NH—CO—NH$_2$, wherein R is hydrogen, hydroxyl, or a lower alkyl having from 1 to 8 carbon atoms selected from the group consisting of methyl, ethyl, propyl, isopropyl, butyl, isobutyl, tert-butyl, pentyl, hexyl, heptyl and octyl. Preferably, the substituted urea is butylurea. The hydrogels of the present invention may further comprise coloring, fragrance or other pharmaceutically acceptable additives. In certain embodiments, the hydrogels of the present invention comprise 50–80% (by weight) methyl cellulose, 15–25% of a natural gum selected from the xanthan and guar gums, 3–7% glucose, 2–3.5% propylparaben, 1.5–3% methylparaben, 1–3% sodium chloride and 0.75–3.5% pectin. Such adhesive hydrogels are described in U.S. Pat. Nos. 5,362,497 and 6,214,374 which are hereby incorporated by reference in their entireties.

The medicament comprises an active ingredient selected from the following, non-limiting, examples of classes pain relief medications: local anesthetics, non-steroidal anti-inflammatory drugs ("NSAID"), opioids, N-methyl-D-aspartate antagonists ("NMDA"), steroids, corticosteroids, tricyclic antidepressants, and mixtures thereof. In certain embodiments, the medicament may comprise analgesics such as lidocaine, trolamine, salicylate, aspirin creams or any suitable prescriptive or non-prescriptive applied analgesic or anesthetic cream.

As used herein, the term "medicament" refers to a composition comprising at least one active ingredient and a pharmaceutically acceptable vehicle suitable for cutaneous application. In certain embodiments, the medicament may further comprise one or more excipients including, but not limited to preservatives, antioxidants, moisturizers, emollients, buffering agents, solubilizing agents, penetration enhancers, skin protectants, and mixtures thereof.

As used herein, the term "local anesthetic" means any drug that provides local numbness or analgesia or any drug that provides a regional blockage of nociceptive pathways (afferent and/or efferent).

Local anesthetics generally act by reversibly interfering with the generation and propagation of impulses along excitable membranes, particularly along nerve axons. More specifically, local anesthetics bind to membrane receptor proteins associated with sodium channels, thereby reducing or obviating the flux of sodium ions across cell membranes through those channels. The consequent reduction or elimination of the sodium ion current obviates the ability of the cell to generate an action potential, thereby preventing propagation of a nerve impulse (see, for example: Luc M. Hondeghem and Ronald D. Miler *Local Anesthetics* in BASIC AND CLINICAL PHARMACOLOGY, 363–70 (Bertram G. Katzung, Ed., Fifth Edition, 1992), and William Catterall and Kenneth Mackie *Local Anesthetics* in GOODMAN & GILMAN'S THE PHARMACOLOGICAL BASIS OF THERAPEUTICS, 331–47 (Perry B. Molinhoff and Raymond W. Ruddon, Eds., Ninth Edition, 1996), which are hereby incorporated by reference in their entireties).

In one embodiment, the medicament comprises at least one local anesthetic as an active ingredient. The local anesthetic can be any local anesthetic known or to be developed. Examples of local anesthetics suitable for use with the invention include: ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, pharmaceutically acceptable salts thereof, and mixtures thereof.

The amide and ester type local anesthetics are preferred. Amide type local anesthetics are characterized by an amide functionality, while ester type local anesthetics contain an ester functionality. Preferred amide type local anesthetics, include lidocaine, bupivacaine, prilocaine, mepivacaine, etidocaine, ropivacaine, dibucaine, and pharmaceutically acceptable salts thereof and mixtures thereof. Preferred ester type local anesthetics include tetracaine, procaine, benzocaine, chloroprocaine, and pharmaceutically acceptable salts thereof and mixtures thereof. The most preferred local anesthetic is lidocaine. Furthermore, in order to improve the effectiveness and tolerance of the present topically effective therapy, local anesthetics with different pharmacodynamics and pharmacokinetics may be combined in a composition of the invention. A preferred combination of local anesthetics is lidocaine and prilocaine and another preferred combination is lidocaine and tetracaine. In certain embodiments the medicament comprises a local anesthetic at a concentration of from about 0.025% to about 50%, from about 0.05% to about 40%, from about 0.1% to about 35%, from about 0.5% to about 30%, and from about 1% to about 25%, by weight.

The medicament of the invention may also comprise as an active ingredient analgesics and anesthetics not typically associated with localized anesthesia, although such compounds can provide a local anesthetic effect. Non-limiting examples of such compounds include non-narcotic analgesics and non-steroidal antinflammatory drugs (NSAID) such as, acetylsalicylic acid, ketoprofen, piroxicam, diclofenac, indomethacin, ketorolac, VIOXX (rofecoxib), CELEBREX (celecoxib), and mixtures thereof.

Non-steroidal antinflammatory drugs generally possess antiinflammatory, antipyretic and analgesic activities. These properties are believed to be mediated through the inhibition of prostaglandin synthesis. More specifically, NSAID compounds have been shown to be inhibitors of either or both of cyclooxygenase I (COX I) or cyclooxygenase II (COX II), which are involved in the synthesis of prostaglandins. Induction of the synthesis of COX II is associated with inflammatory processes and inhibition of COX II is believed to result in the antipyretic and antiinflammatory properties of NSAID compounds. Inhibition of the constitutively-synthesized COX I is believed to be associated with undesirable side effects such as gastric ulcers. Accordingly, selective inhibition of COX II rather than COX I is believed to offer a therapeutic advantage.

The medicaments of the present invention may comprise one or more NSAID compounds as an active ingredient selected from the following, non-limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen; indole and indene acetic acids, including indomethacin, sulindac, and etodolac; heteroaryl acetic acids, including tolmetin, diclofenac, and ketorolac; arylpropionic acids, including ibuprofen, naproxen, flurbiprofen, ketoprofen, fenoprofen, and oxaprozin; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSIDs that may be included within the medicaments employed in the present invention, see Paul A. Insel *Analgesic-Antipyretic and Antiinflammatory Agents and Drugs Employed in the treatment of Gout* in GOODMAN & GILMAN'S THE PHARMACOLOGICAL BASIS OF THERAPEUTICS, 617–57 (Perry B. Molinhoff and Raymond W. Ruddon, Eds., Ninth Edition, 1996), and Glen R. Hanson *Analgesic, Antipyretic and Anit-Inflammatory Drugs* in REMINGTON: THE SCIENCE AND PRACTICE OF PHARMACY VOL II, 1196–1221 (A. R. Gennaro, Ed. 19$^{th}$ Ed. 1995) which are hereby incorporated by reference in their entireties. In another embodiment of the invention, the medicament comprises a mixture of a COX II inhibitor and an inhibitor of 5-lipoxygenase for the treatment of pain and/or inflammation. Suitable COX II inhibitors and 5-lipoxygenase inhibitors, as well as combinations thereof are described in U.S. Pat. No. 6,136,839, which is hereby incorporated by reference in its entirety. In certain embodiments the medicament comprises NSAID at a concentration of from about 0.0001% to about 50%, from about 0.0002% to about 40%, from about 0.0001% to about 30%, from about 0.001% to about 25%, from about 0.01% to about 20%, and from about 0.5% to about 15%, by weight.

As used herein the term "opioid" means all agonists and antagonists of opioid receptors, such as mu (μ), kappa (κ), and delta (δ) opioid receptors and subtypes thereof. For a discussion of opioid receptors and subtypes see *Goodman and Gilman's The Pharmacological Basis of Therapeutics* 9th ed. J. G. Harman and L. E. Limird Eds., McGraw-Hill N.Y.: 1996 pp. 521–555, incorporated herein by reference, in its entirety. Opioids are believed to exert their analgesic properties by inhibiting the release of neurotransmitters, including actylcholin, norepinephrine, dopamine, serotonin, and substance P, which are involved in conduction of nerve impulses (for a further description of suitable opioid analgesics for use in the invention, and their pharmacological mode of action, see, Walter L. Way and E. Leong Way, *Opioid Analgesics & Antagonists* in BASIC AND CLINICAL PHARMACOLOGY, 871–87 (Bertram G. Katzung, Ed., Fifth Edition, 1992), which is hereby incorporated by reference in its entirety). The opioid included within a medicament of the present invention can be any opioid receptor agonist or antagonist known or to be developed. Preferred opioids interact with the μ-opioid receptor, the κ-opioid receptor, or both. Preferably, the opioid is an opioid receptor agonist.

Examples of suitable opioids for use with the invention as an active ingredient include, but are not limited to, alfentanil, allylprodine, alphaprodine, anileridine, benzylmorphine, benzitramide, nor-binaltorphimine, bremazocine, buprenorphine, butorphanol, clonitazene, codeine, CTOP, DAMGO, desomorphine, dextromoramide, dezocine, diampromide, dihydrocodeine, dihydrocodeine enol acetate, dihydromorphine, dimenoxadol, dimepheptanol, dimethylthiambutene, dioxaphetyl butyrate, dipipanone, diprenorphine, DPDPE, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levorphanol, lofentanil, loperamide, meperidine, meptazinol, metazocaine, methadone, metopon, morphine, myrophine, nalbuphine, naltrindole, benzoylhydrazone, naltrexone, narceine, nicomorphine, norlevorphanol, normethadone, nornorphine, norpipanone, opium, oxycodone, oxymorphone, papaveretum, papaverine, pentazocine, phenadoxone, phenazocine, phenoperidine, piminodine, pirtramide, proheptazine, promedol, propiram, propoxyphene, remifentanil, spiradoline, sufentanil, tilidine, U50,488, and U69,593, amiphenazole, cyciazocine, levallorphan, nalmefene, nalorphine, naloxone, naltrexone, pharmaceutically acceptable salts thereof, and mixtures thereof.

Examples of peptide opioids that may be included in the medicament of the invention as an active ingredient include, but are not limited to, Tyr-Gly-Gly-Phe-Leu ([Leu$^5$]enkephalin), Tyr-Gly-Gly-Phe-Met ([Met$^5$]enkephalin), Tyr-Gly-Gly-Phe-Leu-Arg -Arg-Ile-Arg-Pro-Lys-Leu-Lys-Trp-Asp-Asn-Gln (DynorphinA), Tyr-Gly-Gly-Phe-Leu-Arg -Arg-Gln-Phe-Lys-Val-Val-Thr (Dynorphin B), Tyr-Gly-Gly-Phe-Leu-Arg-Lys-Tyr-Pro-Lys (α-Neoendorphin), Tyr-Gly-Gly-Phe-Leu-Arg-Lys-Tyr-Pro (β-Neoendorphin), Tyr-Gly-Gly -Phe-Met-Thr-Ser-Glu-Lys-Ser-Gln-Thr-Pro-Leu-Val-Thr-Leu-Phe-Lys-Asn-Ala-Ile-Ile-Lys -Asn-Ala-Tyr-Lys-Lys-Gly-Glu (β$_h$-Endorphin),[D-Ala$^2$,MePhe$^4$Gly(ol)$^5$] enkephalin (DAMGO),[D-Pen$^2$,D-Pen$^5$]enkephalin (DPDPE),[D-Ser$^2$,Leu$^5$]enkephalin-Thr$^6$ (DSLET),[D-Ala$^2$, D-Leu$^5$]enkephalin (DADL),D-Phe-Cys-Tyr-D-Trp-Orn-Thr-Pen-Thr-NH$_2$(CTOP), [D-Ala$^2$, N-MePhe$^4$,Met(O)$^5$-ol]enkephalin (FK-33824), Tyr-D-Ala-Phe-Asp-Val-Val-Gly -NH$_2$([D-Ala$^2$]Deltorphin 1), Tyr-D-Ala-Phe-Glu-Val-Val-Gly-NH$_2$ ([D-Ala$^2$Glu$^4$]Deltorphin (Deltorphin II)), Tyr-Pro-Phe-Pro-NH$^2$ (Morphiceptin), Tyr-Pro-MePhe-D-Pro-NH$_2$ (PL-017), [D-Ala$^2$,Leu$^5$, Cys$^6$]enkephalin (DALCE), pharmaceutically acceptable salts thereof, and mixtures thereof. Preferred opioids include morphine, loperamide and loperamide derivatives such as those disclosed in U.S. Pat. Nos. 5,763,445; 5,981,513; 5,869,521; 5,744,458; 5,760,023; 5,798,093; 5,849,762; 5,811,078; 6,004,964; 5,962,477; 5,688,955; 5,888,494; 5,646,151; and 5,667,773 (all of which patents are incorporated by reference herein, in their entireties), or pharmaceutically acceptable salts thereof, or mixtures thereof. The most preferred opioid is morphine or a pharmaceutically acceptable salt thereof. In certain embodiments the medicament comprises an opioid at a concentration of from about 0.01% to about 20%, from about 0.02% to about 15%, from about 0.05% to about 10%, from about 0.1% to about 5%, and from about 0.5% to about 2.5%, by weight.

Excitatory neurotransmission is mediated in part by ligand-gated ion channels, and particularly by those cation channels activated by glutamate. There are at least three subtypes of such channels, which are named according to the preferred agonist of the associated receptor. One of these subtypes, accordingly, includes receptors referred to as the N-methly-D-asparate, or NMDA, receptors. A number of antagonists of NMDA receptors have been identified, including dizolcipine (MK-801), remacemide hydrochloride and its metabolites amantadine, budipine, and memantine, dextromethorphan and ketamine. Ketamine, dextromethorphan, and amantadine have been shown to alleviate chronic pain (Fisher et al. (2000), J Pain Symptom Manage 20 (5): 358–73, which is hereby incorporated by reference in its entirety), and ketamine has been shown to improve morphine analgesia (Mercadante et al. J Pain Symptom Manage (2000) 20 (4): 246–52, which is hereby incorporated by reference in its entirety).

Examples of suitable NMDA-receptor antagonists for use with the invention as an active ingredient include, but are not limited to, dextromethorphan ketamine dizolcipine (MK-801), remacemide hydrochloride and its metabolites amantadine, budipine, memantine, and mixtures thereof. In certain embodiments of the present invention, the medicament comprises at least one NMDA-receptor antagonist and at least one opioid compound and/or at least one anti-cholinergic agent such as a tricyclic antidepressants, e.g., amitriptylline (see for example, U.S. Pat. No. 6,197,830, which is hereby incorporated by reference in its entirety). In certain embodiments the medicament comprises a NMDA receptor antagonist at a concentration of from about 0.25% to about 25%, from about 0.5% to about 15%, from about 1% to about 10%, and from about 2% to about 5%, by weight.

In another embodiment of the invention, the medicament further comprises at least one antiinflammatory corticosteroid as an active ingredient. Absorption of topically applied corticosteroid is enhanced significantly (up to 10 fold) using a plastic wrap, such as an impermeable backing film as used in certain embodiments of the present invention. (See, for example, Dirk B. Robinson and Howard I. Miabach, *Dermatologic Pharmacology* in BASIC AND CLINICAL PHARMACOLOGY, 871–87 (Bertram G. Katzung, Ed., Fifth Edition, 1992), which is hereby incorporated by reference in its entirety). Exemplary corticosteroids that are suitable for use as an active ingredient in the medicaments of the present invention include, but are not limited to, the following (a typical, but non-limiting, concentration as weight %, is indicated for each): betamethasone dipropionate (0.05%), diflorasone diacetate (0.05%), halobetasol propionate (0.05%), amcinonide (0.1%), desoximetasone (0.25%), triamcinolone acetonide (0.5%), flucinolone acetonide (0.2%), diflorasone diacetate (0.05%), halcinonide (0.1%), flucinonide (0.05%), and mixtures thereof. In certain embodiments the medicament comprises a steroid or a corticosteroid at a concentration of from about 0.0001% to about 20%, from about 0.0005% to about 15%, from about 0.001% to about 10%, and from about 0.01% to about 5%, by weight.

The major pharmacological activity of tricyclic antidepressants is interference with serotonin and norepinephrine reuptake by neuron terminals. However, some tricyclic antidepressants have other pharmacological effects as well; that is, some tricyclic antidepressants not only relieve symptoms of depressive disorders, but also provide pain relief and muscle relaxation as well (See Lane J. Wallace *Psychopharmaocological Agents* in REMINGTON: THE SCIENCE AND PRACTICE OF PHARMACY VOL II, 1180–95 (A. R. Gennaro, Ed. 19th Ed. 1995); Barkin et al. 2000, Am. J. Ther. 7(1): 31–47; and Lynch 2001, J. Psychiatry Neurosci. 26 (1): 30–36).

In certain embodiments of the present invention, the medicament comprises at least one tricyclic antidepressant, such as, but not limited to imipramine hydrochloride, imipramine pamoate, amitriptyline hydrochloride, amoxapine, desipramine hydrochloride, doxepin, protriptyline hydrochloride, trimipramine, and mixtures thereof, as an active ingredient. In another aspect of this embodiment, the serotoin (5-HT)-norepinephrine uptake inhibitor venlafaxine is also included as the, or one of the, active ingredients in the medicament of the present invention. In certain embodiments the medicament comprises a tricyclic antidepressant at a concentration of from about 0.01% to about 25%, from about 0.05% to about 15%, from about 0.1% to about 10%, and from about 0.5% to about 5%, by weight.

In certain embodiments of the present invention, the medicament comprises at least one excipient selected from the group consisting of preservatives, antioxidants, moisturizers, emollients, buffering agents, solubilizing agents, penetration enhancers, and skin protectants (see, for example, (Monica Ramchandani and Rohinton Toddywala *Formulation of Topical Drug Delivery Systems*, in TRANSDERMAL AND TOPICAL DRUG DELIVERY SYSTEMS, 539–92 (Tapash K. Ghosh, William R. Pfister and Sull Yum, Eds. 1997, which is hereby incorporated by reference in its entirety).

Suitable preservatives for use in the invention and typical concentrations (expressed as weight %) include, but are not limited to: alcohols, including ethanol (>20%), propylene glycol (15%–30%), benzyl alcohol (0.5%–3%) and cholrobutanol (0.5%); quaternary amines including Quaternium 15 (0.02%–0.3%), benzalkonium chloride (0.004%–0.02%), cetrimide (0.2%–0.5%), and imidizolidinyl urea (0.2%); acids including sorbic acid (0.095%–0.2%) and benzoic acid (0.1%–0.5%); parabens such as methyl paraben (0.05%–2%) and propyl paraben (0.002%–0.02%); and phenols including triclosan (0.1%–0.3%), chlorhexidine (0.01%–0.05%), thimerosal (0.002%–0.02%), and mixtures thereof.

Suitable antioxidants for use in the invention and typical concentrations (expressed as w/w %) include, but are not limited to: preferentially oxidized compounds such as ascorbic acid Suitable preservatives and typical concentrations (expressed as w/w %) include, but are not limited to ascorbic acid (0.02%–0.1%), sodium bisulfite (0.1%–0.2%), sodium metabisulfite (0.1%–0.2%) and thiourea (0.005%); propagation terminators such as ascorbic acid esters (0.01%–0.2%), butylated hydroxy anisole (0.005%–0.02%), butylated hydroxy tolune (0.005%–0.02%) and tocopherols (0.05–0.8%); and chelating agents such as EDTA (0.05%–1%), citric acid (0.3–2%), and mixtures thereof.

Suitable moisturizers for use in the invention and typical concentrations (expressed as w/w %) include, but are not limited to: glycerin (0.2%–20%), sorbitol (2%–20%), polyethylene glycols (1%–85%), glucose derivatives (2%–20%), urea (5%–10%), lactic acid (0.5%–5%), propylene glycol (0.5%–50%), and mixtures thereof.

Suitable emollients for use in the invention and typical concentrations (expressed as w/w %) include, but are not limited to: mineral oil(1%–95%), lanolin (1%–10%), isopropyl myristate (1%–10%), isopropyl palmitate (0.5%–6%), vegetable oils (1%–6%), cholesterol (0.3%–5%), stearic acid (1%–20%), stearyl alcohol (1%–10%), cetyl esters wax (1%–15%), and mixtures thereof.

Suitable buffering agents for use in the invention and typical concentrations (expressed as w/w %) include, but are not limited to: anhydrous citric acid (0.3%–2%), lactic acid (0.15%–7%), and mixtures thereof.

Suitable solubilizing agents for use in the invention and typical concentrations (expressed as w/w %) include, but are not limited to: benzalkonium chloride (0.01%–0.02%), benzethonium chloride (0.01%–0.02%), benzyl benzoate (0.01%–4%), β-cyclodextrin (1%–45%), glycerol monstearate (0.5%–5%), lecitihin (0.3%–2.5%), poloxamers (1%–5%), propylene glycol (5%–80%), propylene carbonate (5%–80%), polysorabates (2%–10%), sodium lauryl sulfate (0.0025%–0.025%), sorbitan monolaurate (1%–10%), sorbitan monooleate (1%–10%), sorbitan monopalmitate, sorbitan monostearate (1%–10%), and mixtures thereof.

In certain embodiments, the medicament comprises at least one permeation enhancer to facilitate or enable intradermal and transdermal delivery of one or more active ingredients of the medicament. Permeation enhancers generally chemically modify the skin in a manner that decreases the barrier properties thereof. Preferred permeation enhancers act rapidly and reversibly, are non-toxic, non-allergenic, non-irritating, and are pharmacologically inert (Tapash K. Ghosh and William R. Pfister *Transdermal and Topical Delivery Systems: An Overview and Future Trends*, in TRANSDERMAL AND TOPICAL DRUG DELIVERY SYSTEMS, 1–32 (Tapash K. Ghosh, William R. Pfister and Sull Yum, Eds. 1997, which is hereby incorporated by reference in its entirety). Suitable penetration enhancers for use in the invention and typical concentrations (expressed as w/w %) include, but are not limited to: propylene glycol (5%–80%), alcohols (including ethanol and lauryl alcohol) (0.5%–30%), esters such as glycerol monolaurate (1%–10%), salicylic acid (1%–5%), anionic surfactants such as sodium dodecyl sulfate (1%–10%), cationic surfactants such as cetyltrimethyl ammonium bromide (1%–10%), nonionic surfactants such as polysorbates (1%–10%), phospholipids (1%–10%), urea (1%–5%), and mixtures thereof.

Suitable skin protectants for use in the invention and typical concentrations (expressed as w/w %) include, but are not limited to: allantoin (0.5%–2%), dimethicone (1%–30%), glycerin (20%–45%), petrolatum (30%–90%), zinc oxide (1%–25%), and mixtures thereof.

In other embodiments of the present invention, the medicament comprises more than one active ingredient selected from, but not limited to, the following classes of compounds: opioids, corticosteroids, steroids, NSAID, local anesthetics, tricyclic antidepressants, and NMDA antagonists. In certain embodiments, the medicament comprises one of the following combinations of active ingredients: (a) an opioid and a NMDA antagonist; (b) an opioid and a local anesthetic; (c) a local anesthetic and a NMDA antagonist; (d) a tricyclic antidepressant and a NMDA antagonist. In a particular embodiment of the present invention, the medicament comprises a combination of amitriptyline and ketamine as the active ingredients.

The devices and methods of the present invention are used for the alleviation of pain in a body member by restriction of movement of the body member, application of pressure to acupressure points, and the topical application of a suitable medicament. Accordingly, the methods and devices disclosed herein are used, in non-limiting examples, for the alleviation of pain in the toe, foot, ankle, calf, knee, thigh, hip, finger, knuckle, wrist, forearm, elbow, upper arm, back, shoulder, and neck. Such pain may arise from, but not be limited to, arthritis, muscle strain, tendinitis, and repetitive motion syndromes including carpel tunnel syndrome.

The present invention is not to be limited in scope by the specific embodiments described herein. Indeed, various modifications of the invention, in addition to those described herein will become apparent to those skilled in the art from the foregoing description. Such modifications are intended to fall within the scope of the appended claims.

Various publications and patents are cited herein, the disclosures of which are incorporated by reference in their entireties.

What is claimed is:

1. A device to be disposed around a body portion of a person for treating pain in said body portion comprising:
   a wrap having an interior surface for contacting the body portion, and adapted to be disposed around the body portion,
   said wrap being sufficiently elastic to enable the wrap to be stretched around the body portion to restrict the mobility of the body portion,
   at least one pad section secured to an interior section of the wrap, each pad section adapted to be loaded with medicament,
   at least one nodule extending inwardly from the interior surface of the wrap and adapted to contact and exert pressure at a desired specific location on the body portion, wherein each said nodule is a substantially rigid member having a curved contact surface, and
   means for tightening and adjustably securing the wrap about the body portion, whereby tightening of the wrap causes medicament to exert pressure on and dispense medicament to the area of pain, and to cause the nodule to exert pressure upon the body portion.

2. The device of claim 1 having at least two substantially rigid nodules extending inwardly from the interior surface of the wrap.

3. The device of claim 1 having at least two substantially rigid nodules extending inwardly from the interior surface of the wrap, and located on the wrap such that when the wrap is in place around the body portion, the nodules contact predetermined known acupressure points.

4. The device of claim 1 wherein said curved contact surface is from approximately ¼" to approximately ¾" in diameter.

5. The device of claim 1 wherein the medicament comprises an active ingredient selected from the group consisting of local anesthetics, non-steroidal antiinflammatory drugs, opioids, N-methyl-D-aspartate antagonists, steroids, corticosteroids, tricyclic antidepressants, and mixtures thereof.

6. The device of claim 5, wherein the active ingredient is a local anesthetic selected from the group consisting of ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, lidocaine, bupivacaine, prilocaine, mepivacaine, etidocaine, ropivacaine, dibucaine, procaine, benzocaine, chloroprocaine, pharmaceutically acceptable salts thereof, and mixtures thereof.

7. The device of claim 5, wherein the active ingredient is a non-steroidal antiinflammatory drug selected from the group consisting of acetylsalicylicacid, sodium salicylate, choline magnesium trisalicylate, salsalate, diflunisal, salicylsalicylic acid, sulfasalazine, olsalazin, acetaminophen, indomethacin, sulindac, etodolac, tolmetin, diclofenac, ketorolac, ibuprofen, naproxen, flurbiprofen, ketoprofen, fenoprofen, oxaprozin, mefenamic, meclofenamic acid, piroxicam, tenoxicam, phenylbutazone, oxyphenthartazone, nabumetone, rofecoxib, celecoxib, and mixtures thereof.

8. The device of claim 5, wherein the active ingredient is an opioid selected from the group consisting of opioids for use with the invention as an active ingredient include, but are not limited to, alfentanil, allylprodine, alphaprodine, anileridine, benzylmorphine, benzitramide, nor-binaltorphimine, bremazocine, buprenorphine, butorphanol, clonitazene, codeine, CTOP, DAMGO, desomorphine, dextromoramide, dezocine, diampromide, dihydrocodeine, dihydrocodeine enol acetate, dihydromorphine, dimenoxadol, dimepheptanol, dimethylthiambutene, dioxaphetyl butyrate, dipipanone, diprenorphine, DPDPE, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levorphanol, lofentanil, loperamide, meperidine, meptazinol, metazocaine, methadone, metopon, morphine, myrophine, nalbuphine, naltrindole, benzoylhydrazone, naltrexone, narceine, nicomorphine, norlevorphanol, normethadone, normorphine, norpipanone, opium, oxycodone, oxymorphone, papaveretum, papaverine, pentazocine, phenadoxone, phenazocine, phenoperidine, piminodine, pirtramide, proheptazine, promedol, propiram, propoxyphene, remifentanil, spiradoline, sufentanil, tilidine, U50,488, and U69,593, amiphenazole, cyclazocine, levallorphan, nalmefene, nalorphine, naloxone, naltrexone, Tyr-Gly-Gly-Phe-Leu ([Leu$^5$]enkephalin), Tyr-Gly -Gly-Phe-Met ([Met$^5$] enkephalin), Tyr-Gly-Gly-Phe-Leu-Arg-Arg-Ile-Arg-Pro-Lys-Leu -Lys-Trp-Asp-Asn-Gln (DynorphinA), Tyr-Gly-Gly-Phe-Leu-Arg-Arg-Gln-Phe-Lys -Val-Val-Thr (Dynorphin B), Tyr-Gly-Gly-Phe-Leu-Arg-Lys-Tyr-Pro-Lys (α-Neoendorphin), Tyr-Gly-Gly-Phe-Leu-Arg-Lsy-Tyr-Pro (β-Neoendorphin), Tyr-Gly -Gly-Phe-Met-Thr-Ser-Glu-Lys-Ser-Gln-Thr-Pro-Leu-Val-Thr-Leu-Phe-Lys-Asn-Ala -Ile-Ile-Lys-Asn-Ala-Tyr-Lys-Lys-Gly-Glu ($β_h$-Endorphin), [D -Ala$^2$,MePhe$^4$Gly(ol)$^5$]enkephalin (DAMGO), [D-Pen$^2$, D-Pen$^5$]enkephalin (DPDPE), [D -Ser$^2$,Leu$^5$]enkephalin-Thr$^6$ (DSLET), [D-Ala$^2$,D-Leu$^5$]enkephalin (DADL), D-Phe-Cys -Tyr-D-Trp-Om-Thr-Pen-Thr-NH$_2$(CTOP), [D-Ala$^2$,N-MePhe$^4$,Met(O)$^5$-ol]enkephalin (FK-33824), Tyr-D-Ala-Phe-Asp-Val-Val-Gly-NH$_2$ ([D-Ala$^2$]Deltorphin 1), Tyr-D-Ala -Phe-Glu-Val-Val-Gly-NH$_2$ ([D-Ala$^2$Glu$^4$] Deltorphin (Deltorphin II)), Tyr-Pro-Phe-Pro -NH$^2$ (Morphiceptin), Tyr-Pro-MePhe-D-Pro-NH$_2$ (PL-017), [D -Ala$^2$, Leu⁵,Cys⁶]enkephalin (DALCE), pharmaceutically acceptable salts thereof, and mixtures thereof.

9. The device of claim 5, wherein the active ingredient is a N-methyl-D-aspartate antagonist selected from the group consisting of dextromethorphan, ketamine, dizolcipine (MK-801), remacemide hydrochloride, amantadine, budipine, memantine, and mixtures thereof.

10. The device of claim 5, wherein the active ingredient is a corticosteroid selected from the group consisting of betamethasone dipropionate, diflorasone diacetate, halobetasol propionate, amcinonide, desoximetasone, triamcinolone acetonide, flucinolone acetonide, diflorasone diacetate, halcinonide, flucinonide, and mixtures thereof.

11. The device of claim 5, wherein the active ingredient is a tricyclic antidepressant selected from the group consisting of imipramine hydrochloride, imipramine pamoate, amitriptyline hydrochloride, amoxapine, desipramine hydrochloride, doxepin, protriptyline hydrochloride, trimipramine, and mixtures thereof.

12. The device of claim 1, wherein the medicament comprises at least one excipient selected from the group consisting of preservatives, antioxidants, moisturizers, emollients, buffering agents, solubilizing agents, penetration enhancers, skin protectants, and mixtures thereof.

13. The device of claim 12, wherein the excipient is a preservative selected from the group consisting of ethanol, propylene glycol, benzyl alcohol, choirobutanol, Quaternium 15, benzalkonium chloride, cetrimide, imidizolidinyl urea, sorbic acid, benzoic acid, methyl paraben, and mixtures thereof.

14. The device of claim 12, wherein the excipient is an antioxidant selected from the group consisting of ascorbic acid, sodium bisulfite, sodium metabisulfite, thiourea, ascorbic acid esters, butylated hydroxy anisole, butylated hydroxy tolune, tocopherol, EDTA, citric acid, and mixtures thereof.

15. The device of claim 12, wherein the excipient is a moisturizer selected from the group consisting of glycerin, sorbitol, polyethylene glycol, urea, lactic acid, propylene glycol and mixtures thereof.

16. The device of claim 12, wherein the excipient is an emollient selected from the group consisting of mineral oil, lanolin, isopropyl myristate, isopropyl palmitate, vegetable oil, cholesterol, stearic acid, stearyl alcohol, cetyl ester waxes, and mixtures thereof.

17. The device of claim 12, wherein the excipient is a buffering agent selected from the group consisting of anhydrous citric acid, lactic acid, and mixtures thereof.

18. The device of claim 12, wherein the excipient is a solubilizing agent selected from the group consisting of benzalkonium chloride, benzethonium chloride, benzyl benzoate, β-cyclodextrin, glycerol monstearate lecitihin, a poloxamer, propylene glycol, propylene carbonate, a polysorabate, sodium lauryl sulfate, sorbitan monolaurate, sorbitan monooleate, sorbitan monopalmitate, sorbitan monostearate, and mixtures thereof.

19. The device of claim 12, wherein the excipient is a penetration enhancer selected from the group consisting of propylene glycol, ethanol, lauryl alcohol, glycerol monolaurate, salicylic acid, sodium dodecyl sulfate, cetyltrimethyl ammonium bromide, a polysorbates, a phospholipid, urea, and mixtures thereof.

20. The device of claim 12, wherein the excipient is a skin protectant selected from the group consisting of allantoin, dimethicone, glycerin, petrolatum, zinc oxide, and mixtures thereof.

21. The device of claim 1, wherein the medicament is formulated as a hydrogel.

22. A method of relieving pain in a body portion comprising:
   extending a flexible wrap around the body portion, said wrap
   (i) having an interior surface for contacting the body portion.
   (ii) having a pad section loaded with medicament wherein said pad is attached to the interior surface of the wrap,
   (iii) having at least one substantially rigid nodule extending inwardly from the interior surface of the wrap and adapted to contact at least one pre-located acupressure point near the area of the pain, wherein said nodule has a curved contact surface,
   locating the nodule above the acupressure point, and tightening and adjustably securing the wrap such that mobility of the body portion is decreased, pressure is exerted by the nodule on the desired acupressure point, and medicament is dispensed to the area of pain.

23. The method of claim 22 wherein the wrap comprises at least two nodules, and all of the nodules are located above acupressure points.

24. The method of claim 22, wherein the wrap has at least two substantially rigid nodules, each of which has a curved contact surface of approximately ¼– to approximately ¾ in diameter.

25. The method of claim 22, wherein the medicament comprises an active ingredient selected from the group consisting of local anesthetics, non-steroidal antiinflammatory drugs, opioids, N-methyl-D-aspartate antagonists, steroids, corticosteroids, tricyclic antidepressants, and mixtures thereof.

26. The method of claim 25, wherein the active ingredient is a local anesthetic selected from the group consisting of ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, lidocaine, bupivacaine, prilocaine, mepivacaine, etidocaine, ropivacaine, dibucaine, procaine, benzocaine, chloroprocaine, pharmaceutically acceptable salts thereof, and mixtures thereof.

27. The method of claim 25, wherein the active ingredient is a non-steroidal antiinflammatory drug selected from the group consisting of acetylsalicylicacid, sodium salicylate, choline magnesium trisalicylate, salsalate, diflunisal, salicylsalicylic acid, sulfasalazine, olsalazin, acetaminophen, indomethacin, sulindac, etodolac, tolmetin, diclofenac, ketorolac, ibuprofen, naproxen, flurbiprofen, ketoprofen, fenoprofen, oxaprozin, mefenamic, meclofenamic acid, piroxicam, tenoxicam, phenylbutazone, oxyphenthartazone, nabumetone, rofecoxib, celecoxib, and mixtures thereof.

28. The method of claim 25, wherein the active ingredient is an opioid selected from the group consisting of alfentanil, allylprodine, alphaprodine, anileridine, benzylmorphine, benzitramide, nor-binaltorphimine, bremazocine, buprenorphine, butorphanol, clonitazene, codeine, CTOP, DAMGO, desomorphine, dextromoramide, dezocine, diampromide, dihydrocodeine, dihydrocodeine enol acetate, dihydromorphine, dimenoxadol, dimepheptanol, dimethylthiambutene, dioxaphetyl butyrate, dipipanone, diprenorphine, DPDPE, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levorphanol, lofentanil, loperamide, meperidine, meptazinol, metazocaine, methadone, metopon, morphine, myrophine, nalbuphine, naltrindole, benzoylhydrazone, naltrexone, narceine, nicomorphine, norlevorphanol, normethadone, normorphine, norpipanone, opium, oxycodone, oxymorphone, papaveretum, papaverine, pentazocine, phenadoxone, phenazocine, phenoperidine, piminodine, pirtramide, proheptazine, promedol, propiram, propoxyphene, remifentanil, spiradoline, sufentanil, tilidine, U50,488, and U69,593, amiphenazole, cyclazocine, levallorphan, nalmefene, nalorphine, naloxone, naltrexone, Tyr-Gly-Gly-Phe-Leu ([Leu$^5$]enkephalin), Tyr-Gly -Gly-Phe-Met ([Met$^5$]enkephalin), Tyr-Gly-Gly-Phe-Leu-Arg-Arg-Ile-Arg-Pro-Lys-Leu -Lys-Trp-Asp-Asn-Gln (DynorphinA), Tyr-Gly-Gly-Phe-Leu-Arg-Arg-Gln-Phe-Lys -Val-Val-Thr (Dynorphin B), Tyr-Gly-Gly-Phe-Leu-Arg-Lys-Tyr-Pro-Lys (α-Neoendorphin), Tyr-Gly-Gly-Phe-Leu-Arg-Lsy-Tyr-Pro (β-Neoendorphin), Tyr-Gly -Gly-Phe-Met-Thr-Ser-Glu-Lys-Ser-Gln-Thr-Pro-Leu-Val-Thr-Leu-Phe-Lys-Asn-Ala -Ile-Ile-Lys-Asn-Ala-Tyr-Lys-Lys-Gly-Glu (β$_h$-Endorphin), [D -Ala$^2$,MePhe$^4$Gly(ol)$^5$]enkephalin (DAMGO), [D-Pen$^2$, D-Pen$^5$]enkephalin (DPDPE), [D -Ser$^2$,Leu$^5$]enkephalin-Thr$^6$ (DSLET), [D-Ala$^2$,D-Leu$^5$]enkephalin (DADL), D-Phe-Cys -Tyr-D-Trp-Om-Thr-Pen-Thr-NH$_2$(CTOP), [D-Ala$^2$,N-MePhe$^4$,Met(O)$^5$-ol]enkephalin (FK-33824), Tyr-D-Ala-Phe-Asp-Val-Val-Gly-NH$_2$ ([D-Ala$^2$]Deltorphin 1), Tyr-D-Ala -Phe-Glu-Val-Val-Gly-NH$^2$ ([D-Ala$^2$Glu$^4$] Deltorphin (Deltorphin II)), Tyr-Pro-Phe-Pro -NH$^2$ (Morphiceptin), Tyr-Pro-MePhe-D-Pro-NH$_2$ (PL-017), [D -Ala$^2$, Leu$^5$,Cys$^6$]enkephalin (DALCE), pharmaceutically acceptable salts thereof, and mixtures thereof.

29. The method of claim 25, wherein the active ingredient is a N-methyl-D-aspartate antagonist selected from the group consisting of dextromethorphan, ketamine, dizolcipine (MK-801), remacemide hydrochloride, amantadine, budipine, memantine, and mixtures thereof.

30. The method of claim 25, wherein the active ingredient is a corticosteroid selected from the group consisting of betamethasone dipropionate, diflorasone diacetate, halobetasol propionate, amcinonide, desoximetasone, triamcinolone acetonide, flucinolone acetonide, diflorasone diacetate, halcinonide, flucinonide, and mixtures thereof.

31. The method of claim 25, wherein the active ingredient is a tricyclic antidepressant selected from the group consisting of imipramine hydrochloride, imipramine pamoate, amitriptyline hydrochloride, amoxapine, desipramine hydrochloride, doxepin, protriptyline hydrochloride, trimipramine, and mixtures thereof.

32. The method of claim 22, wherein the medicament comprises at least one excipient selected from the group consisting of preservatives, antioxidants, moisturizers, emollients, buffering agents, solubilizing agents, penetration enhancers, skin protectants, and mixtures thereof.

33. The method of claim 32 wherein the excipient is a preservative selected from the group consisting of ethanol, propylene glycol, benzyl alcohol, cholrobutanol, Quatemium 15, benzalkonium chloride, cetrimide, imidizolidinyl urea, sorbic acid, benzoic acid, methyl paraben, and mixtures thereof.

34. The method of claim 32 wherein the excipient is an antioxidant selected from the group consisting of ascorbic acid, sodium bisulfite, sodium metabisulfite, thiourea, ascorbic acid esters, butylated hydroxy anisole, butylated hydroxy tolune, tocopherol, EDTA, citric acid and mixtures thereof.

35. The method of claim 32 wherein the excipient is a moisturizer selected from the group consisting of glycerin, sorbitol, polyethylene glycol, urea, lactic acid, propylene glycol and mixtures thereof.

36. The method of claim 32 wherein the excipient is an emollient selected from the group consisting of mineral oil, lanolin, isopropyl myristate, isopropyl palmitate, vegetable oil, cholesterol, stearic acid, stearyl alcohol, cetyl ester waxes, and mixtures thereof.

37. The method of claim 32 wherein the excipient is a buffering agent selected from the group consisting of anhydrous citric acid, lactic acid, and mixtures thereof.

38. The method of claim 32 wherein the excipient is a solubilizing agent selected from the group consisting of benzalkonium chloride, benzethonium chloride, benzyl benzoate, β-cyclodextrin, glycerol monstearate lecitihin, a poloxamer, propylene glycol, propylene carbonate, a polysorabate, sodium lauryl sulfate, sorbitan monolaurate, sorbitan monooleate, sorbitan monopalmitate, sorbitan monostearate, and mixtures thereof.

39. The method of claim 32 wherein the excipient is a penetration enhancer selected from the group consisting of propylene glycol, ethanol, lauryl alcohol, glycerol monolaurate, salicylic acid, sodium dodecyl sulfate, cetyltrimethyl ammonium bromide, a polysorbate, a phospholipid, urea, and mixtures thereof.

40. The method of claim 32 wherein the excipient is a skin protectant selected from the group consisting of allanto in, dimethicone, glycerin, petrolatum, zinc oxide, and mixtures thereof.

41. The method of claim 22, wherein the medicament is formulated as a hydrogel.

42. The method of claim 22, wherein the body portion is injured.

* * * * *